United States Patent
Tan et al.

(10) Patent No.: US 12,024,736 B2
(45) Date of Patent: *Jul. 2, 2024

(54) **METHOD FOR DETECTING L-SERINE BASED ON *ESCHERICHIA COLI* CYSTEINE DESULFURASE**

(71) Applicant: Wenzhou Medical University, Zhejiang (CN)

(72) Inventors: Guoqiang Tan, Zhejiang (CN); Jianghui Li, Zhejiang (CN); Feng Liang, Zhejiang (CN); Yilin Pang, Zhejiang (CN)

(73) Assignee: WENZHOU MEDICAL UNIVERSITY, Zhejiang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/814,443

(22) Filed: Jul. 22, 2022

(65) Prior Publication Data

US 2023/0145499 A1 May 11, 2023

(30) Foreign Application Priority Data

Nov. 1, 2021 (CN) .......................... 202111282894.4

(51) Int. Cl.
*C12Q 1/48* (2006.01)
*G01N 33/68* (2006.01)

(52) U.S. Cl.
CPC ........ *C12Q 1/48* (2013.01); *C12Y 208/01007* (2013.01); *G01N 33/6812* (2013.01); *G01N 2333/91194* (2013.01)

(58) Field of Classification Search
CPC .......... C12Q 1/48; C12Q 1/00; C12Y 208/00; C12Y 208/01007; G01N 33/6812; G01N 2333/91194; C12N 9/13
See application file for complete search history.

(56) References Cited

U.S. PATENT DOCUMENTS

2023/0159980 A1* 5/2023 Tan .......................... C12Q 1/48
435/15

OTHER PUBLICATIONS

Binkley F., J. Biol. Chem., 1943, 150, 261-262 (Year: 1943).*
Duan et al. J. Antimicrob. Chemother., 2016, 71, 2192-2199 (Year: 2016).*
Yoshida et el. Analytical Biochemistry, 1993, 208, 296-299 (Year: 1993).*
Das et al. Antioxidants, 2021, 10, 997, 1-27 (Year: 2021).*

* cited by examiner

*Primary Examiner* — Lianko G Garyu
*Assistant Examiner* — Lioubov G Korotchkina
(74) *Attorney, Agent, or Firm* — BUCHANAN INGERSOLL & ROONEY PC

(57) ABSTRACT

The present disclosure provides a method for detecting L-serine based on *Escherichia coli* cysteine desulfurase, and belongs to the technical field of amino acid detection. The method includes the steps of: reacting an unknown sample containing L-serine with *E. coli* cysteine desulfurase in vitro to produce a red substance, and qualitatively or quantitatively determining L-serine content in the unknown sample by observing a color of the red substance or determining content thereof. The method provided by the present disclosure is simple and feasible in technical operation, few in reaction steps, and capable of directly qualitatively detecting by naked eyes and quantitatively detecting the L-serine content.

1 Claim, 2 Drawing Sheets
Specification includes a Sequence Listing.

**METHOD FOR DETECTING L-SERINE BASED ON *ESCHERICHIA COLI* CYSTEINE DESULFURASE**

CROSS REFERENCE TO RELATED APPLICATION(S)

This patent application claims the benefit and priority of Chinese Patent Application No. 202111282894.4, filed on Nov. 1, 2021, the disclosure of which is incorporated by reference herein in its entirety as part of the present application.

REFERENCE TO AN ELECTRONIC SEQUENCE LISTING

The contents of the electronic sequence listing (sequence-listing.xml; Size: 2,363 bytes; and Date of Creation: Jul. 7, 2022) is herein incorporated by reference in its entirety.

TECHNICAL FIELD

The present disclosure relates to the technical field of amino acid detection, in particular to a method for detecting L-serine based on *Escherichia coli* cysteine desulfurase.

BACKGROUND ART

L-serine is a non-essential polar amino acid in the human body. It is mainly involved in the biosynthesis of proteins in the body. It is also an important precursor of purines, pyrimidines, and phospholipids. It plays an important role in immune regulation, tumor metabolism and other processes, and is expected to serve as a tumor marker of some cancers. In terms of medicinal use, L-serine is widely used in amino acid infusions and nutritional additives, and its derivatives also have excellent medicinal value and biological activity. In terms of cosmetic industry, L-serine is extensively added to high-grade cosmetics due to its wettability and moisture retention. With the in-depth research and understanding of L-serine and the continuous development of medical and health care, the demand for L-serine is also increasing. Therefore, providing a quick and easy detection method for determining the content of L-serine in mixed amino acids, especially a detection technology capable of eliminating the interference of D-serine, cycloserine, serine analogs and serine derivatives, is extremely important for the development and utilization of L-serine.

At present, methods for determining amino acid content inside and outside of China are mainly divided into instrumental methods, chromogenic methods, chemiluminescence methods, and enzymatic methods. Instrumental methods usually include HPLC, GC-MS, LC-MS, NMR, and automatic amino acid analyzer. The chromogenic methods include chromotropic acid-spectrophotometry, paper chromatography-spectrophotometry, and ninhydrin method. Chemiluminescence method is mainly capillary electrophoresis coupling with electrochemiluminescence. Enzymatic methods include serine aminotransferase method and cystathionine lyase method.

Among them, instrumental methods such as liquid chromatography, gas chromatography, and chromatography-mass spectrometry have good sensitivity and high accuracy, but require expensive equipment, specialized laboratories, professionally trained laboratory technicians, high maintenance costs, and relatively high laboratory consumables. As the most basic and traditional detection method, ninhydrin method is easy to operate and quick to react, but it has high requirements on reaction conditions, and requires precise control of reaction temperature, pH, and time. Moreover, the method has different sensitivities to different types of amino acids and is not suitable for analysis of samples that require high precision. Fluorescence quenching method can avoid the interference of most amino acids, but the sample needs to undergo complex phosphorylation pretreatment, and the detection result has a large error. The paper chromatography-spectrophotometry is easy to operate, but it is not suitable for the analysis and detection of large quantities of samples due to its poor stability. Chromotropic acid-spectrophotometry has fast reaction speed, simple operation, and high accuracy, but poor anti-interference ability.

Enzymatic methods have excellent specificity and accuracy, but the currently used enzymatic methods have many reaction steps and many factors that affect the determination, and the detection signal often cannot be directly observed or directly measured. Therefore, it is very necessary to develop an enzymatic method for determining L-serine which is simple and can be directly observed with the naked eye after the reaction.

SUMMARY

An objective of the present disclosure is to provide a method for detecting L-serine based on *E. coli* cysteine desulfurase. The method is simple and feasible in technical operation, few in reaction steps, and capable of directly qualitatively detecting by naked eyes and quantitatively detecting the L-serine content.

To achieve the above objective, the present disclosure provides the following solution:

The present disclosure provides a method for detecting L-serine based on *E. coli* cysteine desulfurase, including the steps of: reacting an unknown sample containing L-serine with *E. coli* cysteine desulfurase in vitro to produce a red substance, and qualitatively or quantitatively determining L-serine content in the unknown sample by observing a color of the red substance or determining content thereof.

Preferably, a method for qualitatively detecting the L-serine content in the unknown sample may be implemented by: observing whether a stable red substance is produced after the reaction, and a color depth of the red substance with the naked eye, and qualitatively determining the presence or absence of the L-serine in the unknown sample and the content thereof.

Preferably, a method for quantitatively detecting the L-serine content in the unknown sample may include:
  measuring an absorbance of an L-serine standard solution, and constructing a standard curve; and
  measuring an absorbance of a reacted red substance, and substituting the absorbance into an equation of the standard curve to quantitatively obtain the L-serine content in the unknown sample.

Preferably, both the absorbance of the L-serine standard solution and the absorbance of the red substance may be measured at a wavelength of 528 nm.

Preferably, the *E. coli* cysteine desulfurase may have an amino acid sequence shown in SEQ ID NO: 1.

Preferably, the unknown sample and the *E. coli* cysteine desulfurase may be mixed and reacted in equal volumes.

Preferably, a reaction time may be 60-180 min.

The present disclosure provides the following technical effects:

According to the method for detecting L-serine based on *E. coli* cysteine desulfurase provided by the present disclosure, because the *E. coli* cysteine desulfurase takes L-cysteine as a substrate to catalyze the generation of L-alanine and elemental sulfur, and the purified cysteine desulfurase binds to the prosthetic group pyridoxal phosphate, it appears yellow with the naked eye, and there is a characteristic absorption peak at 395 nm when scanned by a UV-Vis spectrophotometer. According to the inventor's previous research, it is easy to know that the enzyme is expressed in an IscA⁻/SufA⁻ double-deficient bacterium. The enzyme turns red when observed with the naked eye, and there is a stable characteristic absorption peak at 528 nm when scanned by the UV-Vis spectrophotometer. After a large number of experiments, a stable red substance may also be generated by in vitro reaction of IscA⁻/SufA⁻ double-deficient *E. coli*-derived cysteine desulfurase with the L-serine, and specificity thereof depends on the L-serine. More importantly, the depth of the red color, the level of the absorption peak at 528 nm, and the L-serine added in the reaction mixture are dose-dependent, thus realizing the qualitative and quantitative determination of the L-serine in an unknown sample. The detection method provided by the present disclosure features convenient technical operation and few reaction steps. Not only can the detection method achieve intuitive qualitative detection and precise quantification, but also can effectively prevent the interference of D-serine, cycloserine, serine analogs and other amino acids, providing a scientific method for the rapid detection of L-serine in different fields.

BRIEF DESCRIPTION OF THE DRAWINGS

In order to more clearly illustrate the examples of the present disclosure or the technical solution in the prior art, the accompanying drawings required in the examples will be briefly introduced below. Obviously, the drawings in the following description are only some examples of the present disclosure. For those of ordinary skill in the art, other drawings can also be obtained according to these drawings without creative efforts.

DETAILED DESCRIPTION OF THE EMBODIMENTS

The technical solution of the present disclosure will now be specifically described by way of examples, which should not be construed as limiting the present disclosure, but should be understood as a more detailed description of certain aspects, characteristics and embodiments of the present disclosure.

The test methods used in the following examples are conventional, unless otherwise specified; the materials and reagents used are commercially available reagents and materials, unless otherwise specified.

*E. coli* cysteine desulfurase used in the following examples has an amino acid sequence shown in SEQ ID NO: 1:

MELPIYLDYSATTPVDPRVAEKMMQFMTMDGTFGNPASRSHRFGWQAEEA

VDIARNQIADLVGADPREIVFTSGATESDNLAIKGAANFYQKKGKHIITS

-continued

KTEHKAVLDTCRQLEREGFEVTYLAPQRNGIIDLKELEAAMRDDTILVSI

MHVNNEIGVVQDIAAIGEMCRARGIIYHVDATQSVGKLPIDLSQLKVDLM

SFSGHKIYGPKGIGALYVRRKSRVRIEAQMHGGGHERGMRSGTLPVHQIV

GMGEAYRIAKEEMATEMERLRGLRNRLWNGIKDIEEVYLNGDLEHGAPNI

LNVSFNYVEGESLIMALKDLAVSSGSACTSASLEPSYVLRALGLNDELAH

SSIRFSLGRFTTEEEIDYTIELVRKSIGRLRDLSPLWEMYKQGVDLNSIE

WAHHHHHH

Example 1 Method for Qualitative/Semi-Quantitative Detection of L-Serine Based on *E. coli* Cysteine Desulfurase 1. Reagents
A. 1 M L-serine standard solution;
B. Reaction buffer: 40 mM Tris-HCl buffer (pH 9.0), 100 µM *E. coli* cysteine desulfurase, and 0.4 mM L-cysteine;
2. The L-serine standard solution was diluted to five concentrations, respectively: A: 0.00 mM, B: 0.25 mM, C: 0.50 mM, D: 1.00 mM, E: 2.00 mM. Each serial dilution of the standard solution and the unknown sample (100 µL) were each mixed with 100 µL of reaction buffer, incubated at room temperature (25° C.) for 2 h, observed with the naked eye, and photographed, and a standard colorimetric card was established.

Figure 1:
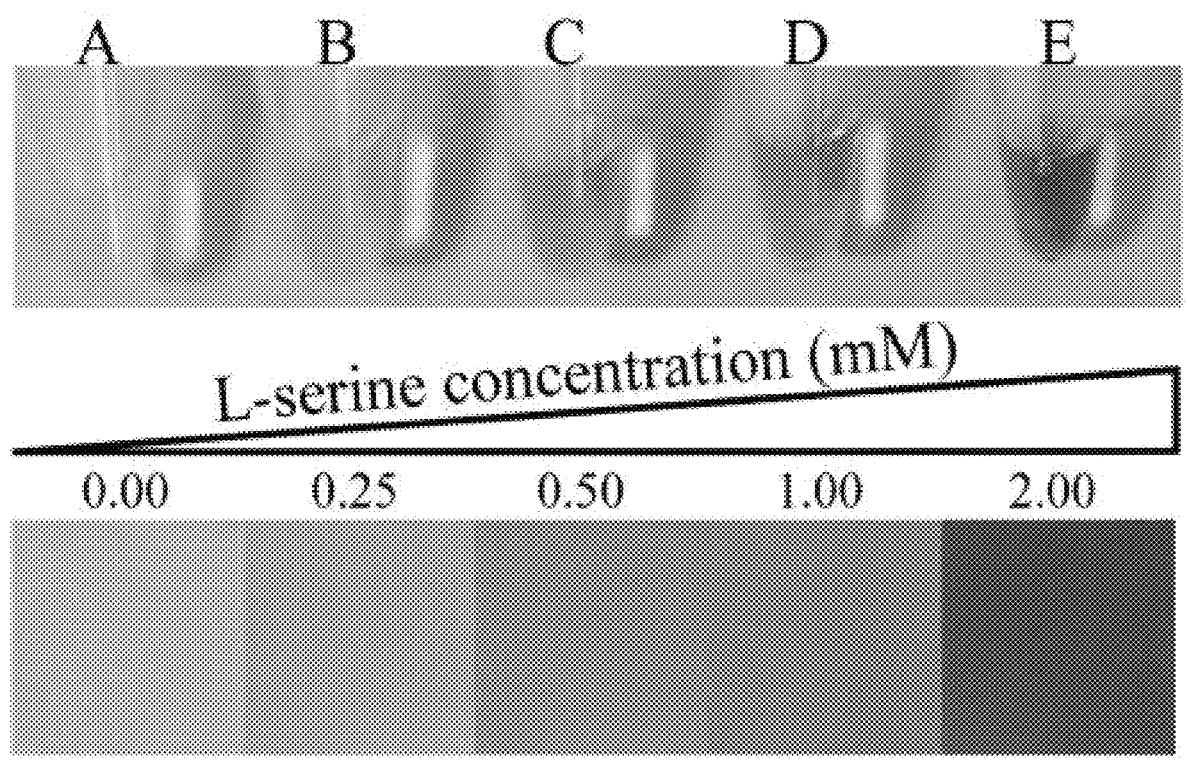
FIG. 1 is an illustrative diagram of qualitative and semi-quantitative determination of L-serine and a standard colorimetric card.

As shown in FIG. 1, in the concentration range of 0 to 2 mM, the color after enzymatic reaction of the L-serine standard solution with the reaction buffer changed from light yellow to light pink and gradually darkened to red. By observing with the naked eye, this color change has good discrimination, and different colors and their depths can reflect the presence or absence of L-serine well, as well as the level of concentration. It can be seen that the experimental method for qualitative/semi-quantitative detection of L-serine of the present disclosure is feasible, convenient and efficient.

Example 2 Method for Quantitatively Detecting L-Serine Based on *E. coli* Cysteine Desulfurase 1. Reagents
A. 1 M L-serine standard solution;
B. Reaction buffer: 40 mM Tris-HCl buffer (pH 9.0), 100 µM *E. coli* cysteine desulfurase, and 0.4 mM L-cysteine.
2. Determination of an Optimal Reaction Time and Linear Range
A. Determination of a Reaction Time
L-serine to be tested was mixed with the reaction buffer in equal volumes, and incubated at 25° ° C. for different times; the absorbance was measured at a wavelength of 528 nm; a curve was plotted with the time as the horizontal axis and the absorbance value at 528 nm as the longitudinal axis.
B. Determination of the Optimal Linear Range
The L-serine standard solution was diluted to three concentrations, respectively: 0.50 mM, 1.00 mM, and 2.00 mM. Each serial dilution of the standard solution and the unknown sample (100 µL) were each mixed with 100 µL of reaction buffer, incubated at room temperature (25° C.) for 2 h, and the absorbance at 528 nm was measured for sample and standard tubes, respectively.

3. Plotting of a Standard Curve

A standard curve was plotted with the concentration of the standard solution as the abscissa and the absorbance measured at a wavelength of 528 nm as the ordinate, and the curve was fitted to obtain a curve equation and an $R^2$ value.

4. Determination of L-Serine Content in Samples

The L-serine concentration was obtained according to the standard curve equation obtained above and the absorbance value of the sample tube.

Figure 2:
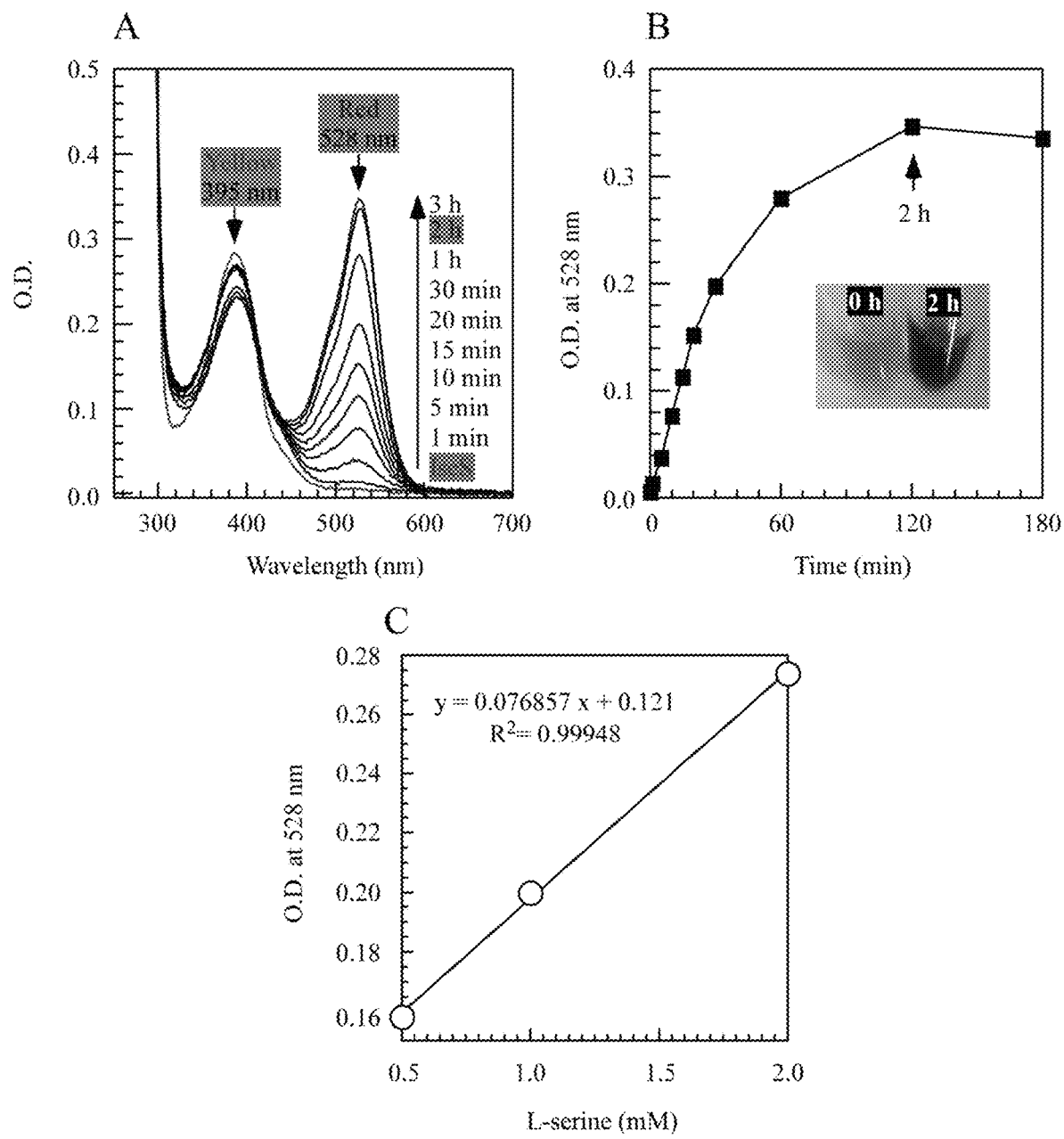
FIG. 2 illustrates optimization of incubation time and establishment of a standard curve; A: effects of incubation time and wavelength on enzymatic reaction; B: screening of optimal incubation time; C: standard curve.

As shown in FIG. 2, with the prolongation of the incubation time between the L-serine standard and the reaction buffer, the absorption peak at 528 nm, which represents red, appears from nothing and gradually increases (FIG. 2A). The absorption peak reaches the highest at 2 h, and plateaus within 1 h (FIG. 2B). It can be seen that the optimal incubation time is 2 h, and as determined according to the optimized incubation time, the plotted standard curve has a good linear range in the range of 0.5 to 2.0 mM (FIG. 2C). It can be seen that the experimental method for quantitatively detecting L-serine provided by the present disclosure is feasible.

Example 3 Determination of the Ability to Resist Other L-Amino Acids

500 μL each of L-serine and other L-amino acids (4 mM) to be tested were mixed with 500 μL of *E. coli* cysteine desulfurase, respectively, and incubated on a shaker at 37° C. and 250 rpm for 2 h, and the color depth was observed with the naked eye and photographed.

The results show that only L-serine and *E. coli* cysteine desulfurase appear red after incubation, and other amino acids and the control without amino acid appear light yellow, indicating that the method provided by the present disclosure can directly observe whether the red color is produced or not and determine whether L-serine is contained, and it is easy to know that this method has better resistance to the interference of other L-amino acids and better specificity. In addition, the inventors have further confirmed through experiments that the detection method has good anti-interference ability for D-serine, cycloserine and serine derivatives. The above results show the method provided by the present disclosure is feasible to qualitatively detect L-serine, and the operation is simple and feasible, with excellent specificity.

Example 4 Determination of L-Serine Content in L-Serine Accumulating Strain IscA⁻/SufA⁻ Double Knockout Strain 1. Culture of IscA/SufA Double Knockout Strain IscA⁻/sufA⁻ double mutant strain (for the construction method, refer to the master's thesis "*Functions of IscA and SufA in the Biogenesis of Iron-Sulfur Clusters in Escherichia coli*" from TONG Zhenzhen) and control wild-type *E. coli* MC4100 were cultured in LB broth at 250 rpm (round per minute) and 37° C. overnight, and the bacterial suspension cultured overnight was diluted 1:50 into Erlenmeyer flasks containing 500 mL of freshly prepared LB broth, respectively; the culture was continued under the same conditions until the $OD_{600\ nm}$ reached 0.6 (logarithmic growth phase), and the bacteria were harvested by centrifugation.

2. Metabolite Extraction

The above *E. coli* cells were sampled, 50 mL of pre-cooled methanol/acetonitrile/water (2:2:1, v/v/v) was added to each sample, vortexed to mix, sonicated in an ice bath for 20 min, and incubated at −20° C. for 1 h to precipitate the protein; the protein was centrifuged at 14,000 rpm and 4° C. for 20 min, and the supernatant was collected and dried in vacuum. During detection, 100 μL of buffer (40 mM Tris-HCl, pH 9.0) was added to reconstitute, centrifuged at 14,000 rcf and 4° C. for 20 min, and the supernatant was collected.

3. Determination of Sample Concentration

The supernatant in step 2 and L-serine standard were taken and incubated with the reaction buffer for 2 h, respectively; pictures were taken and the absorbance at 528 nm was measured; a standard curve was plotted, and the sample concentration was calculated.

Macroscopically, compared with the control without L-serine (light yellow), the extract of wild-type MC4100 turned pale pink after reacting with the reaction buffer (compared with the colorimetric card, it was judged that the L-serine concentration was between 0.00 and 0.25 mM), and the extract of the iscA⁻/sufA⁻ double mutant strain turned dark pink after reacting with the reaction buffer (compared with the colorimetric card, it was judged that the L-serine concentration was between 0.50 and 1 mM); as calculated by quantitative determination, the L-serine content in the extract of the wild-type MC4100 was 0.21 mM. The L-serine content of the extract of the iscA⁻/sufA⁻ double mutant strain was 0.53 mM. It can be seen that the results of the two methods are consistent.

The above examples are only intended to describe the preferred implementation of the present disclosure and not intended to limit the scope of the present disclosure. Various alterations and improvements made by those of ordinary skill in the art based on the technical solution of the present disclosure without departing from the design spirit of the present disclosure shall fall within the scope of the appended claims of the present disclosure.

```
Sequence Listing Information:
DTD Version: V1_3
File Name: SEQUENCE LISTING.xml
Software Name: WIPO Sequence
Software Version: 2.0.0
Production Date: 2022-07-04
General Information:
Current application/Applicant file reference: HLP20220302223
Earliest priority application/IP Office: CN
Earliest priority application/Application number: 202111282894.4
Earliest priority application/Filing date: 2021-11-01
```

-continued
Applicant name: Wenzhou Medical University
Applicant name/Language: en
Invention title: METHOD FOR DETECTING L-SERINE BASED ON *ESCHERICHIA COLI* CYSTEINE DESULFURASE (en)
Sequence Total Quantity: 1
Sequences:
Sequence Number (ID): 1
Length: 408
Molecule Type: AA
Features Location/Qualifiers:
-source, 1..408
>mol_type, protein
>note, amino acid sequence of E. coli cysteine desulfurase
>organism, synthetic construct
Residues:
```
MELPIYLDYS ATTPVDPRVA EKMMQFMTMD GTFGNPASRS HRFGWQAEEA VDIARNQIAD   60

LVGADPREIV FTSGATESDN LAIKGAANFY QKKGKHIITS KTEHKAVLDT CRQLEREGFE  120

VTYLAPQRNG IIDLKELEAA MRDDTILVSI MHVNNEIGVV QDIAAIGEMC RARGIIYHVD  180

ATQSVGKLPI DLSQLKVDLM SFSGHKIYGP KGIGALYVRR KSRVRIEAQM HGGGHERGMR  240

SGTLPVHQIV GMGEAYRIAK EEMATEMERL RGLRNRLWNG IKDIEEVYLN GDLEHGAPNI  300

LNVSFNYVEG ESLIMALKDL AVSSGSACTS ASLEPSYVLR ALGLNDELAH SSIRFSLGRF  360

TTEEEIDYTI ELVRKSIGRL RDLSPLWEMY KQGVDLNSIE WAHHHHHH            408
END
```

What is claimed is:

1. A method for detecting L-serine in an unknown sample with *Escherichia coli* cysteine desulfurase, comprising the steps of:

reacting the unknown sample with *Escherichia coli* cysteine desulfurase in vitro;

observing a color of a resulting reaction solution to determine whether a stable red substance is produced after the reaction;

observing a color depth of the red substance with naked eyes; and qualitatively determining the presence or absence of the L-serine in the unknown sample and an L-serine content of the unknown sample;

wherein if the red substance is present, the L-serine content in the unknown sample is quantitatively determined by a process comprising:

measuring absorbances of L-serine standard solutions after reacting the solutions with *Escherichia coli* cysteine desulfurase to produce the red substance;

constructing a standard curve based on the absorbances of the L-serine standard solutions;

measuring an absorbance of the unknown sample; and substituting the absorbance of the unknown sample into an equation of the standard curve to quantitatively obtain the L-serine content in the unknown sample;

wherein the reacting of the L-serine standard solutions and the unknown sample with *Escherichia coli* cysteine desulfurase occurs for a reaction time of 60-180 min;

wherein the absorbances of the L-serine standard solutions and the unknown sample are measured at a wavelength of 528 nm; and wherein the *Escherichia coli* cysteine desulfurase has the amino acid sequence of SEQ ID NO: 1.

* * * * *

SEQUENCE LISTING

```
Sequence total quantity: 1
SEQ ID NO: 1             moltype = AA   length = 408
FEATURE                  Location/Qualifiers
source                   1..408
                         mol_type = protein
                         note = amino acid sequence of E. coli cysteine desulfurase
                         organism = synthetic construct
SEQUENCE: 1
MELPIYLDYS ATTPVDPRVA EKMMQFMTMD GTFGNPASRS HRFGWQAEEA VDIARNQIAD    60
LVGADPREIV FTSGATESDN LAIKGAANFY QKKGKHIITS KTEHKAVLDT CRQLEREGFE   120
VTYLAPQRNG IIDLKELEAA MRDDTILVSI MHVNNEIGVV QDIAAIGEMC RARGIIYHVD   180
ATQSVGKLPI DLSQLKVDLM SFSGHKIYGP KGIGALYVRR KSRVRIEAQM HGGGHERGMR   240
SGTLPVHQIV GMGEAYRIAK EEMATEMERL RGLRNRLWNG IKDIEEVYLN GDLEHGAPNI   300
LNVSFNYVEG ESLIMALKDL AVSSGSACTS ASLEPSYVLR ALGLNDELAH SSIRFSLGRF   360
TTEEEIDYTI ELVRKSIGRL RDLSPLWEMY KQGVDLNSIE WAHHHHHH               408
```